United States Patent
Maitland et al.

(10) Patent No.: US 9,918,855 B2
(45) Date of Patent: Mar. 20, 2018

(54) ROBUST ADAPTABLE FOOT PROSTHESIS

(71) Applicant: University of Washington, Seattle, WA (US)

(72) Inventors: Murray E. Maitland, Seattle, WA (US); Katherine M. Steele, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 15/154,515

(22) Filed: May 13, 2016

(65) Prior Publication Data

US 2016/0331559 A1    Nov. 17, 2016

Related U.S. Application Data

(60) Provisional application No. 62/161,791, filed on May 14, 2015.

(51) Int. Cl.
*A61F 2/66* (2006.01)
*A61F 2/50* (2006.01)

(52) U.S. Cl.
CPC .............. *A61F 2/6607* (2013.01); *A61F 2/66* (2013.01); *A61F 2002/5018* (2013.01); *A61F 2002/5072* (2013.01); *A61F 2002/6614* (2013.01); *A61F 2002/6621* (2013.01); *A61F 2002/6642* (2013.01)

(58) Field of Classification Search
CPC .................................................. A61F 2/6607
See application file for complete search history.

(56) References Cited

U.S. PATENT DOCUMENTS

| | | | | |
|---|---|---|---|---|
| 5,674,296 A | * | 10/1997 | Bryan | A61B 17/686 606/247 |
| 6,187,052 B1 | * | 2/2001 | Molino | A61F 2/6607 623/47 |
| 8,118,873 B2 | * | 2/2012 | Humphreys | A61F 2/442 623/17.16 |
| 2003/0199981 A1 | * | 10/2003 | Ferree | A61F 2/4425 623/17.15 |
| 2005/0043800 A1 | * | 2/2005 | Paul | A61B 17/1757 623/17.15 |
| 2007/0083267 A1 | * | 4/2007 | Miz | A61F 2/4425 623/17.13 |
| 2008/0109084 A1 | * | 5/2008 | Maitland | A61F 2/586 623/21.15 |
| 2012/0078313 A1 | * | 3/2012 | Hasse | A61F 2/442 606/305 |

* cited by examiner

*Primary Examiner* — Jacqueline Woznicki
(74) *Attorney, Agent, or Firm* — McDonnell Boehnen Hulbert & Berghoff LLP

(57) ABSTRACT

A device is provided to allow adaptation of a prosthetic or robotic foot in the medial-lateral direction, including pronation and supination of the foot using a series of articulations. Articulations are permitted in the disclosed device due to linkage systems positioned at various locations of the prosthetic foot. In particular, the device includes multiple connected linkage systems each including upper and lower portions with an articulating contact surface designed for load carriage and stability. The point of contact between the contact surfaces of each linkage system comprises the position-dependent instantaneous center of rotation of the upper portion with respect to the lower portion. The device also includes a platform coupled between the linkage systems and a base.

20 Claims, 11 Drawing Sheets

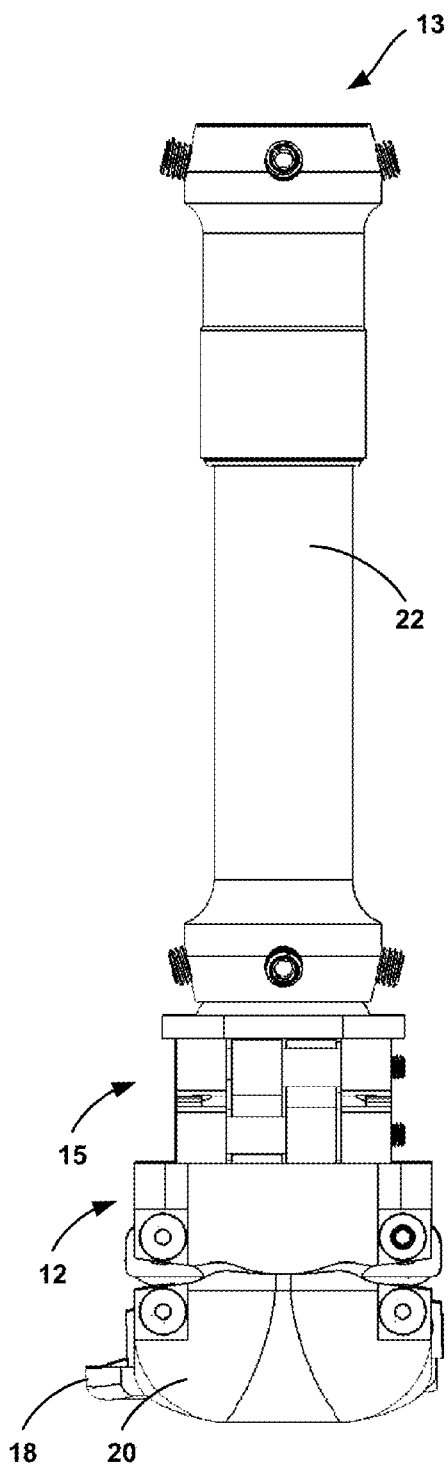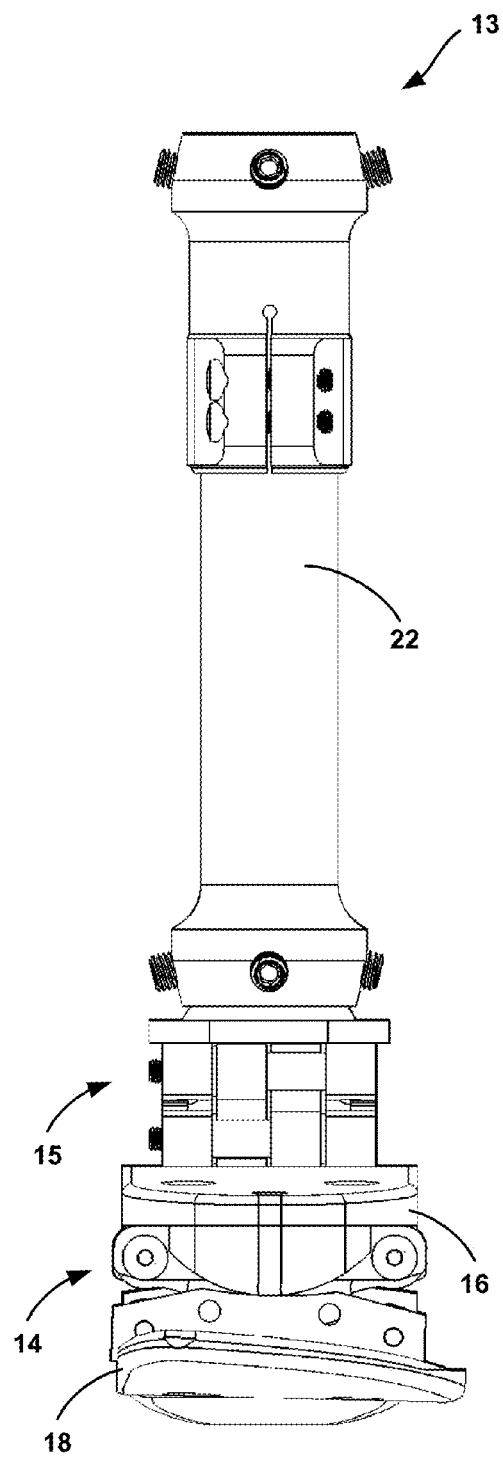
Fig. 12
Fig. 13

ROBUST ADAPTABLE FOOT PROSTHESIS

CROSS-REFERENCE TO RELATED APPLICATIONS

This application claims the benefit of the filing date of U.S. Provisional Patent Application Ser. No. 62/161,791, filed May 14, 2015, which is hereby incorporated by reference in its entirety.

BACKGROUND

Unless otherwise indicated herein, the materials described in this section are not prior art to the claims in this application and are not admitted to be prior art by inclusion in this section.

In the normal ankle and foot there is an anatomical chain of movement from the ankle joint to the toes. In particular, a normal foot has a series of articulations with increasing levels of motion, including the talocrural (ankle) joint, the subtalar (heel) joint, the tarsal (midfoot) joint, and the metatarsals and phalanges (forefoot). The sequence of the articulations of a normal foot permits variations in lateral motions depending on the surface coming into contact with the foot, or the position of the body above the foot. When lower extremity amputations result due to abnormal development, trauma, diabetes, or some other medical condition, these amputations of the leg or ankle result in chronic disability. This is because conventional prosthetic foot designs do not sufficiently replace the anatomical function of the foot to accommodate sideways motions. As such, mediolateral stresses remain a significant problem with current prosthetics, especially on slide-slopes, uneven ground, turning, or where there is uncertainty of placement of the foot such as during cognitive tasks while ambulating.

Pain and skin breakdown at the residual limb remains a problem in current prosthetics in part because of shear stresses induced by forces on the socket. Skin breakdown may cause limitations in many activities of daily living. Additionally, gait is an attention-demanding task, and any concurrent cognitive task, even a very simple one, may disrupt walking performance. The current mechanical designs of existing prostheses are believed to be related to back pain, residual limb pain, and contralateral knee pain along with early osteoarthritis. As a result, many aspects of an individual's physical performance are chronically affected with use of a prosthetic device, not only those associated with walking. If physical activity is reduced, chronic diseases such as cardiovascular disease or impaired glucose metabolism are at increased risk.

SUMMARY

Example devices described herein allow adaptation of a prosthetic foot in the medial-lateral direction, including pronation and supination of the prosthetic foot. The device described herein may mimic the functions of a normal foot using a series of articulations. Articulations are permitted in the disclosed devices due to linkage systems positioned at various locations of the prosthetic foot, as described in more detail below. The disclosed devices may improve walking, running, and other forms of bipedal motion (such as dancing) for people with prosthetic feet. In particular, the disclosed devices may allow for level placement of the leg over the foot on uneven ground or a medial-lateral grade during walking and running. The disclosed devices may further accommodate variations in leg position over the foot for a person with poor coordination. In addition, the disclosed devices may permit variations in leg position on a level surface for people participating in various recreational activities such as dance or racquet sports. Legged robotic devices may also benefit from the mechanical adaptations of the invention to make them more versatile and functional traversing variable terrain.

Thus, in one aspect, a device is provided including (a) a first linkage system and a second linkage system, each linkage system including (i) a first upper portion having a first contact surface, (ii) a first lower portion having a second contact surface, wherein the second contact surface contacts the first contact surface, (iii) a first tension bearing element with a first end pivotally coupled to a first end of the first lower portion and a second end pivotally coupled to a second end of the first upper portion, and (iv) a second tension bearing element with a first end pivotally coupled to a second end of the first lower portion and a second end pivotally coupled to a first end of the first upper portion, (b) a platform coupled to one of the first upper portion or the first lower portion of the first linkage system and further coupled to the first upper portion of the second linkage system, and (c) a base coupled to the first lower portion of the second linkage system.

In a second aspect, the device may further include (d) a third linkage system, including (i) a third upper portion having a third contact surface, (ii) a third lower portion having a fourth contact surface, wherein the fourth contact surface contacts the third contact surface, (iii) a third tension bearing element with a first end pivotally coupled to a first end of the third lower portion and a second end pivotally coupled to a second end of the third upper portion, and (iv) a fourth tension bearing element with a first end pivotally coupled to a second end of the third lower portion and a second end pivotally coupled to a first end of the third upper portion, wherein the first upper portion of the first linkage system is coupled to the platform and the third lower portion of the third linkage system is coupled to one of the platform or the first upper portion of the first linkage system, and wherein the plane of rotation of the third upper portion of the third linkage system is perpendicular to the plane of rotation of the first upper portion of the first and second linkage systems.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 12 is a rear view of the prosthetic device, according to the example embodiment of FIG. 10.

FIG. 13 is a front view of the prosthetic device, according to the example embodiment of FIG. 10.

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, with respect to measurements, "about" means +/−5%.

Standing atop a typical artificial leg without medial-lateral accommodation to the ground surface is analogous to standing on stilts. The long lever-arm of the leg makes it such that the center of mass of the body falls outside of the base of support without much angle of the leg with respect to the base. Example devices described herein may allow adaptation of a prosthetic foot in the medial-lateral direction, including pronation and supination of the prosthetic foot. The devices described herein may mimic the functions of a normal foot using a series of articulations. The articulations may be permitted via linkage systems positioned at various locations of the prosthetic foot, as described in more detail with reference to the figures below.

Figure 1:
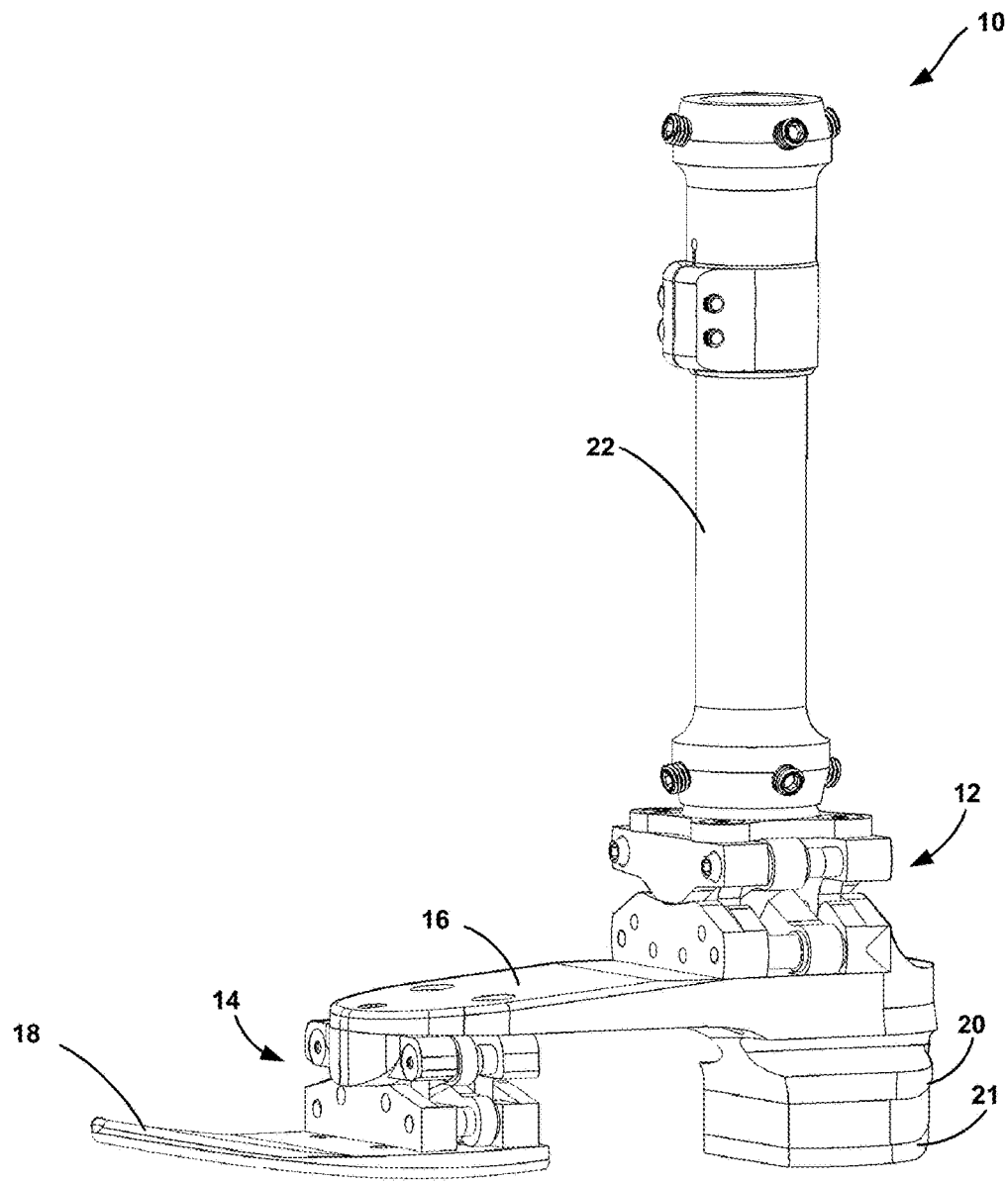
FIG. 1 is a perspective view of a prosthetic device, according to one example embodiment.

In a first aspect, FIG. 1 illustrates an example prosthetic device 10 in accordance with one embodiment of the invention. The prosthetic device 10 may include a first linkage system 12 and a second linkage system 14. The first linkage system 12 may be an ankle linkage component of the prosthetic device 10, and the second linkage system 14 may be a forefoot linkage component. The plane of rotation of the first linkage system 12 may be substantially parallel to the plane of rotation of the second linkage system 14. In other words, like components of the first linkage system 12 and the second linkage system 14 are facing the same direction, as shown in FIG. 1. The prosthetic device 10 may also include a platform 16 coupling the first linkage system 12 to the second linkage system 14. The prosthetic device 10 may further include a base 18 coupled to a lower portion of the second linkage system 14.

Figure 2:
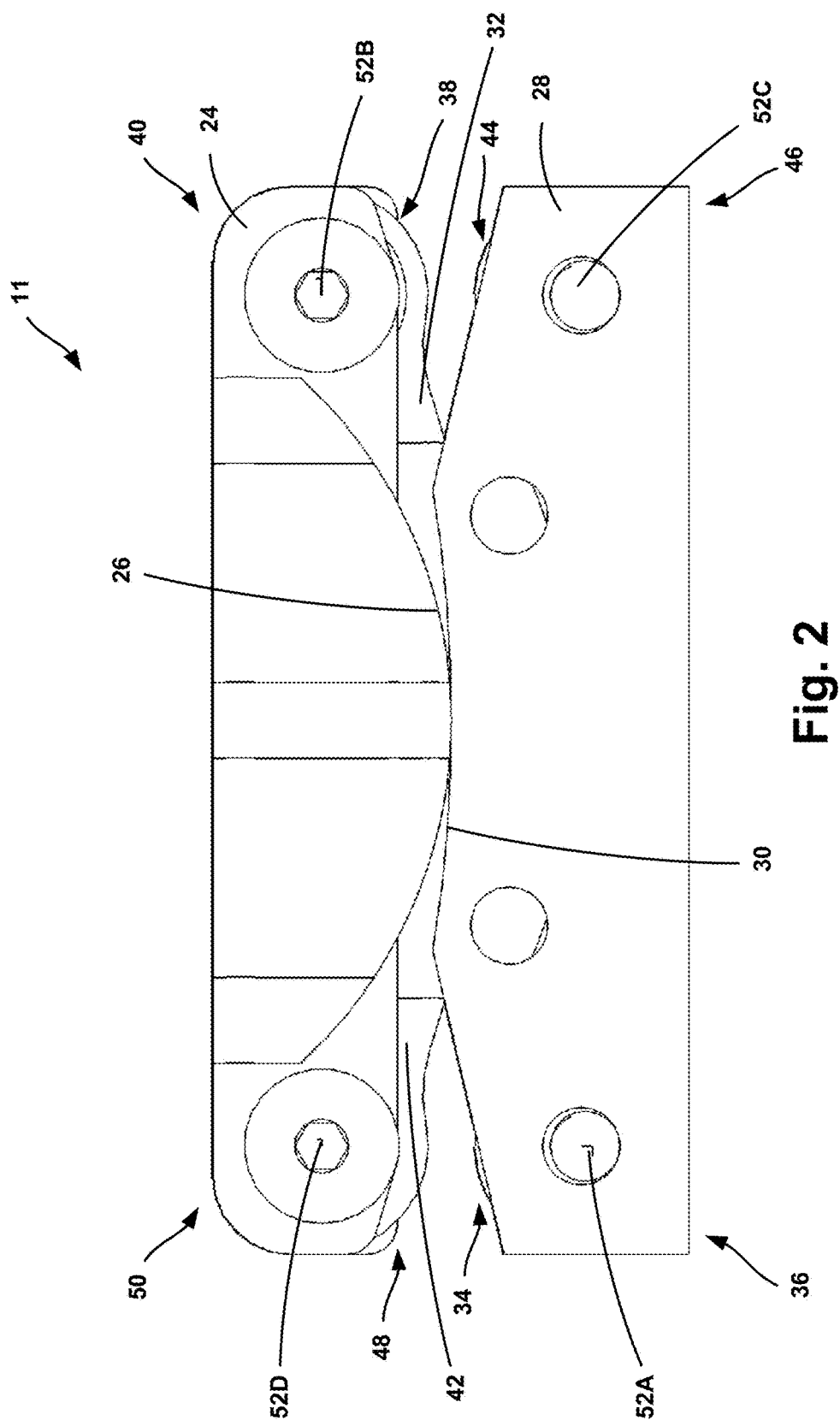
FIG. 2 is a side view of an example linkage system of the prosthetic device, according to an example embodiment.
Figure 3:
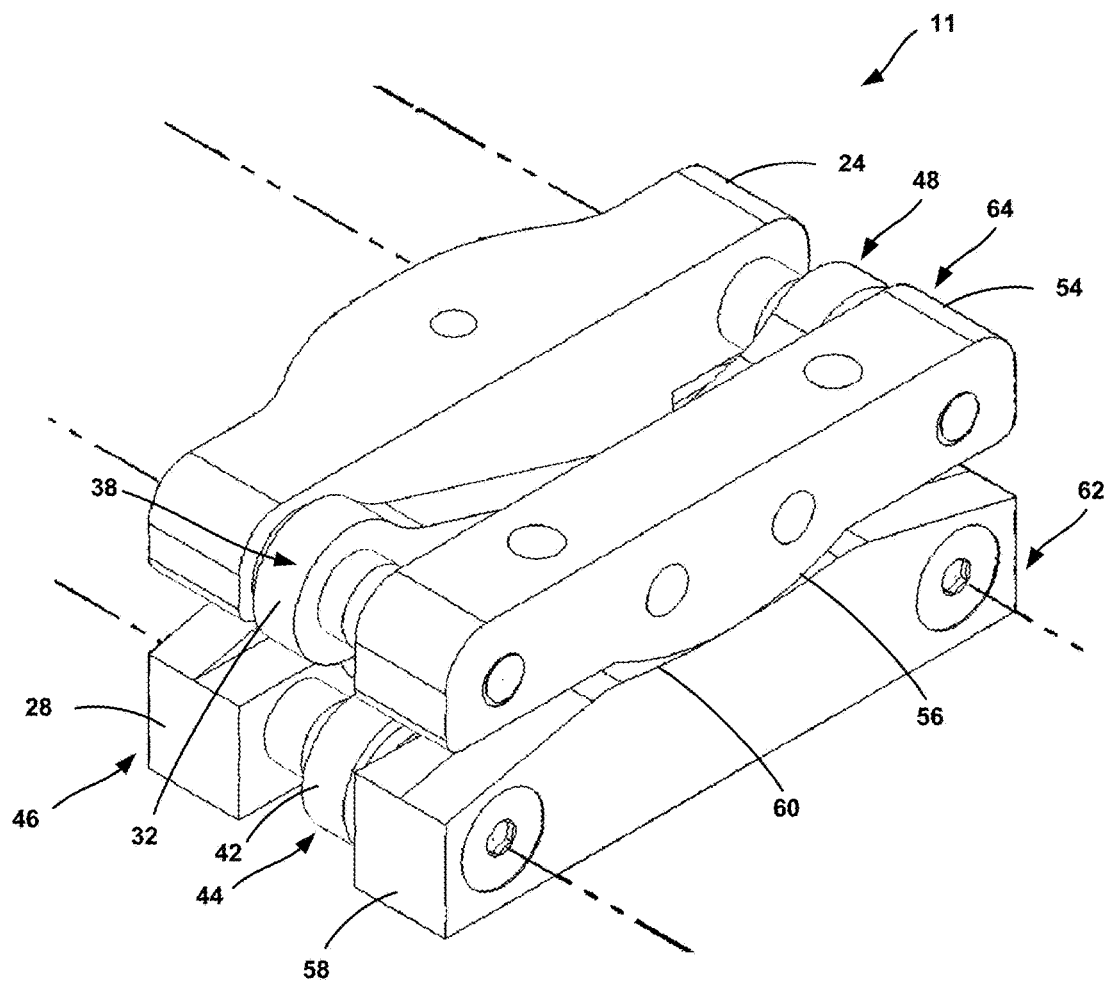
FIG. 3 is a perspective view of the example linkage system, according to the example embodiment of FIG. 2.
Figure 4:
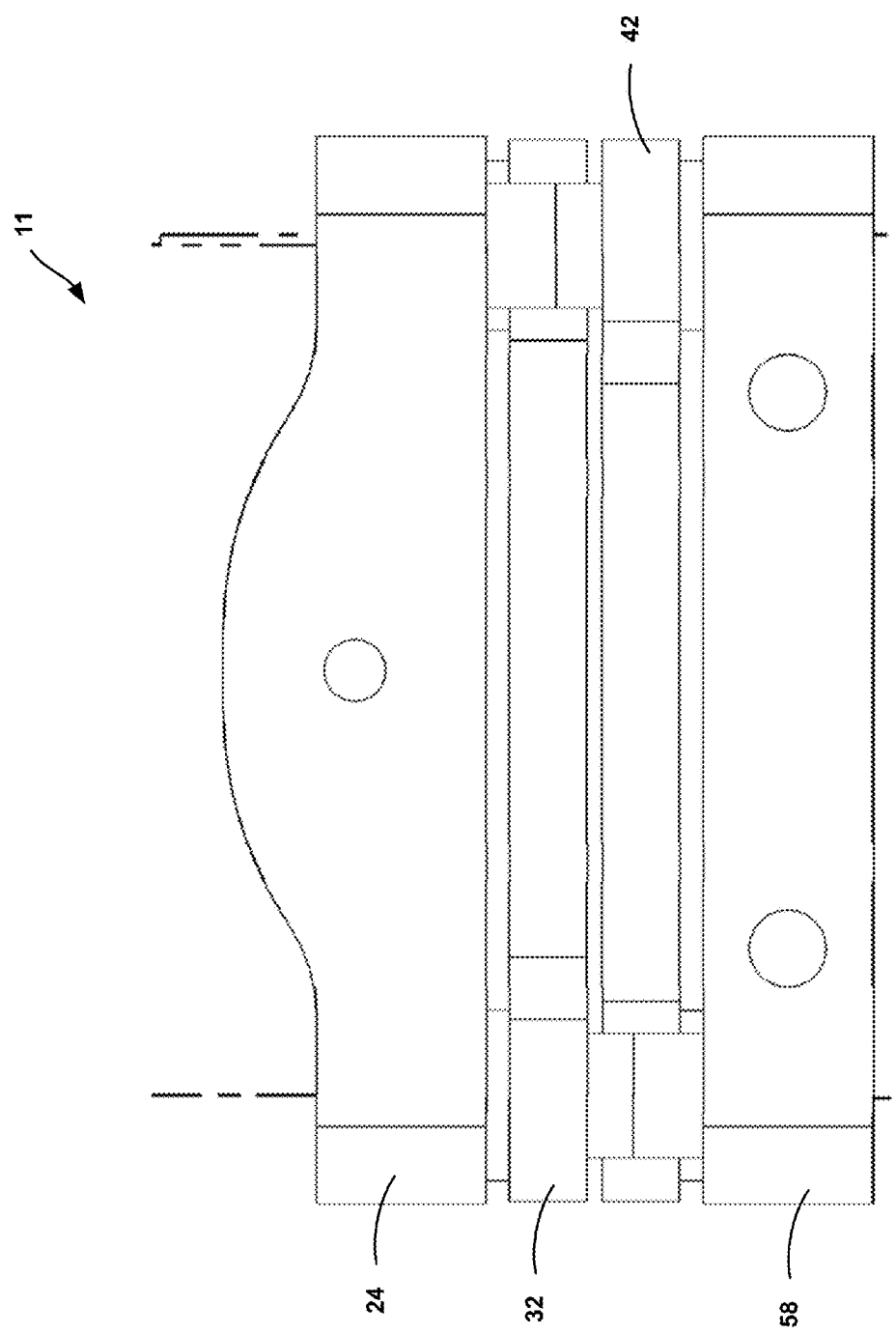
FIG. 4 is a top view of the example linkage system, according to the example embodiment of FIG. 2.

FIG. 2 illustrates a side view of an example linkage system 11 of the prosthetic device 10. FIG. 3 illustrates a perspective view of the linkage system 11 of FIG. 2, and FIG. 4 illustrates a top view of the linkage system 11 of FIG. 2. The first linkage system 12, the second linkage system 14, and other linkage systems described herein may be configured similarly to the linkage system 11 shown in FIGS. 2-6. In particular, as shown in FIG. 2, the linkage system 11 may include a first upper portion 24 having a first contact surface 26. The linkage system 11 may further include a first lower portion 28 having a second contact surface 30, where the second contact surface 30 contacts the first contact surface 26. In particular, as shown in FIG. 2, the first contact surface 26 of the linkage system 11 comprises a convex surface, and the second contact surface 30 of the linkage system 11 comprises a concave surface.

In one example, the first contact surface 26 comprises a first material, and the second contact surface 30 comprises a second material that is different than the first material. In one particular example, the first contact surface comprises aluminum, stainless steel, or titanium, while the second contact surface comprises polyoxymethylene, polyethylene, or nylon. Other examples are possible as well. In one example, the entire first upper portion 24 may comprise the materials described above for the first contact surface 26. In another example, the first upper portion 24 is coated with a different material at the first contact surface 26, such that the material at the first contact surface 26 is different than the material of the rest of the first upper portion 24. Similarly, in one example the entire first lower portion 28 may comprise the materials described above for the second contact surface 30. In another example, the first lower portion 28 is coated with a different material at the second contact surface 30, such that the material at the second contact surface 30 is different than the material of the rest of the first lower portion 28.

The linkage system 11 further includes a first tension bearing element 32 with a first end 34 pivotally coupled to a first end 36 of the first lower portion 28 and a second end 38 pivotally coupled to a second end 40 of the first upper portion 24. The linkage system 11 further includes a second tension bearing element 42 with a first end 44 pivotally coupled to a second end 46 of the first lower portion 28 and a second end 48 pivotally coupled to a first end 50 of the first upper portion 24. In one example, the first tension bearing element 32 and/or the second tension bearing element 42 may be a rigid bar or other rigid component capable of receiving tensile and compressive forces. In another example, the first tension bearing element 32 and/or the second tension bearing element 42 may be a cable or such component capable of receiving tensile forces, but not compressive forces.

The first end 34 of the first tension bearing element 32 may be pivotally coupled to the first end 36 of the of the first lower portion 28 via axle 52A, and the second end 38 of the first tension bearing element 32 may be pivotally coupled to the second end 40 of the first upper portion 24 via axle 52B. The axles 52A, 52B may be configured to pass through a corresponding hole in the first lower portion 28 and first upper portion 24, respectively, and corresponding holes in the first tension bearing element 32. Similarly, the first end 44 of the second tension bearing element 42 may be pivotally coupled to the second end 46 of the first lower portion 28 via axle 52C, and the second end 48 of the second tension bearing element 42 may be pivotally coupled to the first end 50 of the first upper portion 24 via axle 52D. The axles 52C, 52D may be configured to pass through a corresponding hole in the first lower portion 28 and first upper portion 24, respectively, and corresponding holes in the second tension bearing element 42.

In one example, the linkage system 11 may further include a third tension bearing element with a first end pivotally coupled to the first end 36 of the first lower portion 28 and a second end pivotally coupled to the second end 40 of the first upper portion 24, and a fourth tension bearing element with a first end pivotally coupled to a second end 46 of the first lower portion 28 and a second end pivotally coupled to a first end 50 of the first upper portion 24. In such an example, the linkage system 11 includes a pair of opposing tension bearing elements on each side of the first upper portion and first lower portion.

In another example, such as the example shown in FIG. 3, the linkage system may further include a second upper portion 54 having a third contact surface 56, and a second lower portion 58 having a fourth contact surface 60. The third contact surface 56 contacts the fourth contact surface 60. In particular, the third contact surface 56 of the linkage system 11 comprises a convex surface, and the fourth contact surface 60 of the linkage system 11 comprises a concave surface. Further, the first end 34 of the first tension bearing element 32 is pivotally coupled to a first end 62 of the second lower portion 58 and a second end 38 of the first tension bearing element 32 is pivotally coupled to the second end 40 of the first upper portion 24. Further, the first end 44 of the second tension bearing element 42 is pivotally coupled to the second end 46 of the first lower portion 28 and the second end 48 of the second tension bearing element 42 is pivotally coupled to the first end 64 of the second upper portion 54. Other arrangements are possible as well.

In one embodiment, the linkage system 11 includes at least one spring mechanism configured to return the linkage system 11 to a position of repose when the device is unweighted. In one example, the spring mechanism comprises a compliant material disposed between the first upper portion 24 and the first lower portion 28 and/or between the second upper portion 54 and the second lower portion 58. In another example, the spring mechanism comprises an actuator disposed between the first upper portion 24 and the first lower portion 28 and/or between the second upper portion 54 and the second lower portion 58. The at least one spring mechanism may be configured to transition the linkage system 11 from a weighted height to an unweighted height. For example, in operation a wearer of the prosthetic device 10 may step on an inclined surface at an angle to the incline, as discussed in more detail below in relation to FIGS. 5 and 6. In such a case, on one side of the linkage system 11, the first lower portion 28 moves closer to the first upper portion 24. At the same time on the opposite side of the linkage system 11, the first upper portion 24 moves further away from the first lower portion 28. As the wearer lifts the device 10 off of the inclined surface, the at least one spring mechanism may return or assist with returning the linkage system 11 to a position of repose before the wearer places the foot back on the ground. Further, the at least one spring mechanism may be used to modify rotational properties of the first lower portion 28 with respect to the first upper portion 24.

The length-to-height ratio of the linkage system 11 may vary. In one example, the length-to-height ratio may be greater than 1.5:1. For example, the length-to-height ratio of the linkage system may be 2:1, or 3:1. It may be desirable to keep the center of rotation of the linkage system 11 relatively low, so as to keep the center of rotation within the base of support at the maximal angular position. The physical size of the linkage system 11 is scalable within the desired length-to-height ratio.

As discussed above, each of the first linkage system 12 and the second linkage system 14 described above, and the third linkage system described below may have each of the components of linkage system 11. However, the linkage systems may be slightly different from one another. For example, the second linkage system 14 may have a shorter length and shorter height than the length and height of the first linkage system 12. Such a configuration may be advantageous for fitting the prosthetic device 10 in a shoe or other housing, as examples. In another example, each of the linkage systems may have varying length to height ratios to match their desired function in the prosthetic device 10. As another example, each linkage system may have a defined maximum rotation to better mimic their corresponding joints of a human foot. The at least one spring mechanism may be used to define the maximum rotation for each linkage system. In another example, the structure of the linkages themselves may define the maximum angle of rotation. In one example, the maximum angle between the first upper portion 24 of the first linkage system 12 and the first lower portion 28 of the first linkage system 12 may be between about ten and twenty degrees. As another example, the maximum angle between the first upper portion 24 of the second linkage system 14 and the first lower portion 28 of the second linkage system 14 may be between about twenty and forty-five degrees.

As discussed above, the prosthetic device 10 may also include a platform 16 coupling the first linkage system 12 to the second linkage system 14. In particular, as shown in FIG. 1, the first lower portion 28 of the first linkage system 12 may be coupled to a top surface of the platform 16, and the first upper portion 24 of the second linkage 14 may be coupled to a bottom surface of the platform 16. The platform 16 may include carbon fiber, a carbon fiber composite, a high density nylon material, polyoxymethylene, or combinations thereof, amongst other possibilities. In one example, the platform 16 may be a flexible bridging platform coupling the first linkage system 12 to the second linkage system 14. In another example, the platform 16 may be a rigid brace, a bar, and/or a span coupling the first linkage system 12 to the second linkage system 14. In either case, the platform 16 may mimic a tarsal joint (midfoot) of a normal foot to supply a balance of rigidity and spring to the foot function.

As weight moves from hindfoot to forefoot, the platform 16 accommodates unevenness between the front and back ground level, as well as the angle of the user's leg relative to the floor. As the wearer of the prosthetic device 10 shifts their weight forward, the platform 16 may act as a springboard propelling the wearer forward in bipedal motion. In one example, the platform 16 may have a level bottom surface, such that the first upper portion 24 of the first linkage system 12 and the top surface of the hindfoot support 20 are substantially parallel. In another example, the platform 16 may have a two-tiered bottom surface. The two-tiered bottom surface of the platform 16 may cause the height of the second linkage system 14 to be less than the height of the hindfoot support 20. Such a configuration may be advantageous for fitting the prosthetic device 10 in a shoe, as an example. The preferred position of the two-tiered bottom surface of the platform 16 may be adjusted based on the particular user, and the particular footwear of the user. For example, higher heeled shoes will need more angulation of the two-tiered bottom surface. Other configurations are possible as well.

As discussed above, the prosthetic device 10 may further include a base 18 coupled to a lower portion of the second linkage system 14. The base 18 may include a forefoot pad coupled to the first lower portion 28 of the second linkage system 14 and a flexible toe pad extending from the first lower portion 28 of the second linkage system 14 in a direction away from the first linkage system 12. The base 18 may include carbon fiber, a carbon fiber composite, a high density nylon material, polyoxymethylene, or combinations thereof, among other possibilities. As shown in FIG. 1, the first linkage system 12 may be coupled to a hindfoot support 20. In particular, an upper surface of the hindfoot support 20 may be coupled to the platform 16, while a lower surface of the hindfoot support 20 may be coupled to a hindfoot pad 21. The hindfoot pad 21 may include a rounded end to ease bipedal motion and accommodate a user's heel strike against the ground surface.

In one example, a prosthetic limb 22, such as a shank, may be coupled to the platform 16, in a position above the first linkage system 12. A bottom portion of the prosthetic limb 22 may include a connector portion that is configured to mate with a connector portion positioned on the platform 16. In another embodiment, the device 10 may be coupled to a robotic device, such as a leg of a legged robotic device. Other connection mechanisms are possible as well.

The prosthetic device 10 may further include a housing sized and shaped to receive the prosthetic device 10. For example, the housing may be a shoe that encompasses the prosthetic device 10. In another example, the housing may be shaped like a human foot. Other examples are possible as well.

Figure 5:
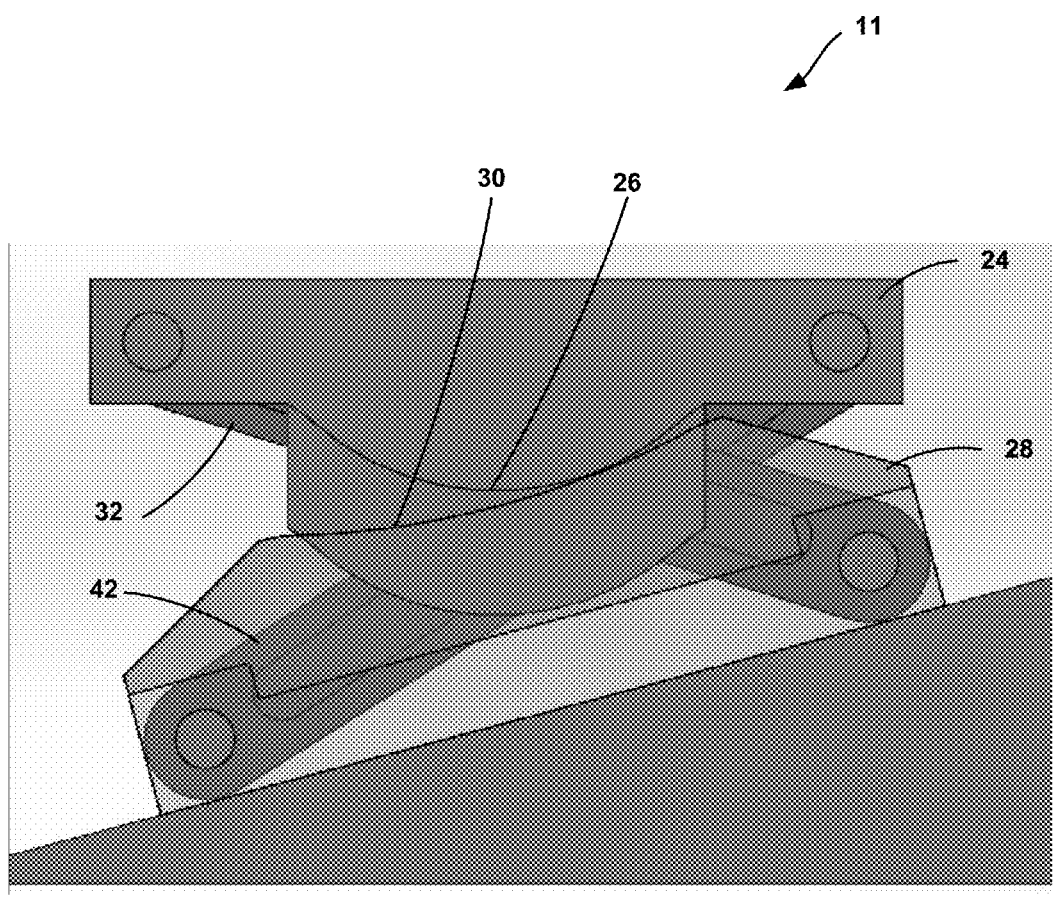
FIG. 5 shows the linkage system of FIG. 2 on an incline, according to the example embodiment of FIG. 2.

FIG. 5 illustrates the linkage system 11 on a medial-lateral grade, according to an example embodiment. As the base 18 and hindfoot pad 20 contacts uneven ground, the first lower portion 28 of the first linkage system 12 and of the second linkage system 14 rotate, and becomes parallel to the ground surface. At the same time, the first upper portion 24 of the first linkage system 12 and of the second linkage system 14 remain perpendicular to the prosthetic limb 22. As the first upper portion 24 rotates with respect to the first lower portion 28, the first contact surface 26 remains in contact with the second contact surface 60. In particular, the contact between the first contact surface 26 and the second contact surface 30 of each linkage system comprises an instantaneous center of rotation of the first upper portion 24 with respect to the first lower portion 28. The instantaneous center of rotation is the point fixed to a body undergoing planar movement that has zero velocity at a particular instant of time. At this instant, the velocity vectors of the trajectories of other points in the body generate a circular field around this point which is identical to what is generated by a pure rotation. As such, each linkage system described herein includes a weight-bearing surface that follows the instantaneous center of rotation of the linkage system. The surface geometry of the first contact surface 26 and/or the second contact surface 30 of each linkage system described herein may be determined by the instantaneous center of rotation of the linkage system. As such, the point of contact between the contact surfaces of each linkage system comprises the position-dependent instantaneous center of rotation of the first upper portion 24 with respect to the first lower portion 28. With such a configuration, side-to-side motion with balance and stability is maintained because the position of the center of rotation varies with the applied forces.

Figure 6:
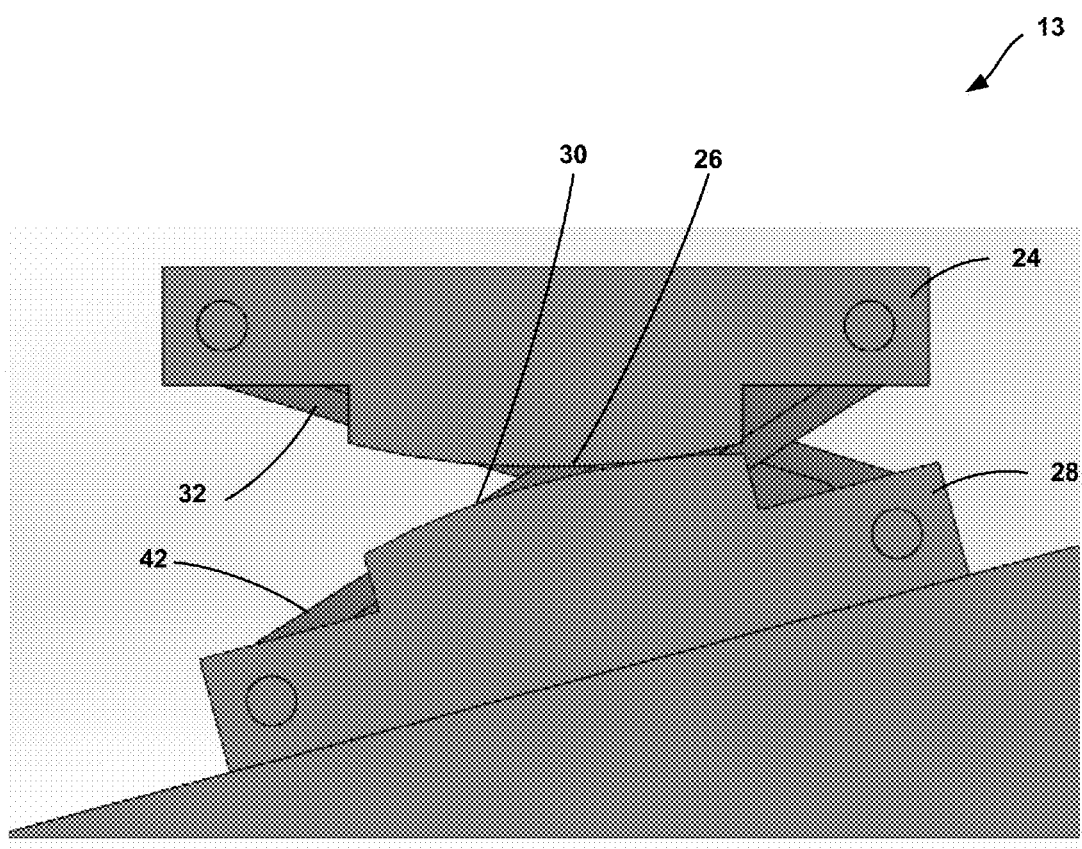
FIG. 6 shows another example linkage system on an incline, according to an example embodiment.

FIG. 6 shows another example linkage system 13 on a medial-lateral grade, according to an example embodiment. The linkage system 13 may be substantially the same as linkage system 11, with the exception of the second contact surface 30 of the first lower portion 28. As such, the linkage system 13 may be used as the first linkage system 12, the second linkage system 14, and/or the third linkage system. As shown in FIG. 6, the first contact surface 26 of the linkage system 13 comprises a convex surface, and the second contact surface 30 of the linkage system 13 also comprises a convex surface. As the base 18 and hindfoot pad 20 contacts uneven ground, the first lower portion 28 of the linkage system 13 rotate, and becomes parallel to the ground surface. At the same time, the first upper portion 24 of the linkage system 13 remains perpendicular to the prosthetic limb 22. As the first upper portion 24 rotates with respect to the first lower portion 28, the first contact surface 26 remains in contact with the second contact surface 60.

Thus, using one or more of the linkage systems described in FIGS. 5 and 6, the prosthetic device 10 may help individuals having poor balance and gait. For example, the ground may be even but the prosthetic device 10 may come in contact with the ground at an angle due to poor balance and gait of the user. If the prosthetic device 10 contacts the ground in the medial-lateral direction, the first lower portion 28 of the first linkage system 12 and the second linkage system 14 rotates, and becomes parallel to the ground surface, while the first upper portion 24 of the first linkage system 12 and the second linkage system 14 remains perpendicular to the prosthetic limb 22. In the embodiment including a third linkage system, if the prosthetic device 10 contacts the ground in a dorsiflexion or plantarflexion position, the third lower portion of the third linkage system may rotate, and become parallel to the inclined ground surface, while the third upper portion of the third linkage system may remain perpendicular to the prosthetic limb 22.

Figure 7:
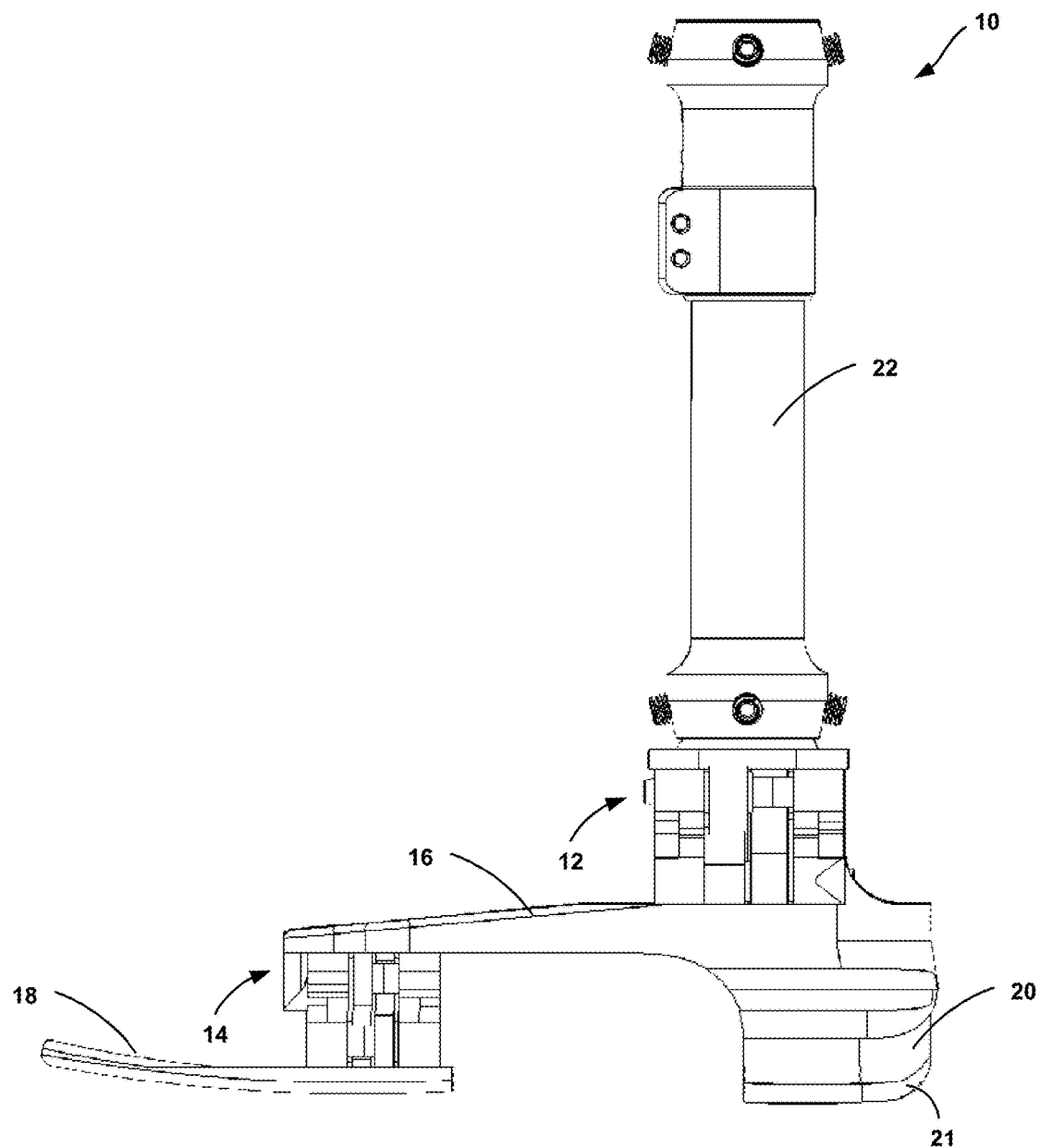
FIG. 7 is a side view of the prosthetic device, according to the example embodiment of FIG. 1.
Figure 8:
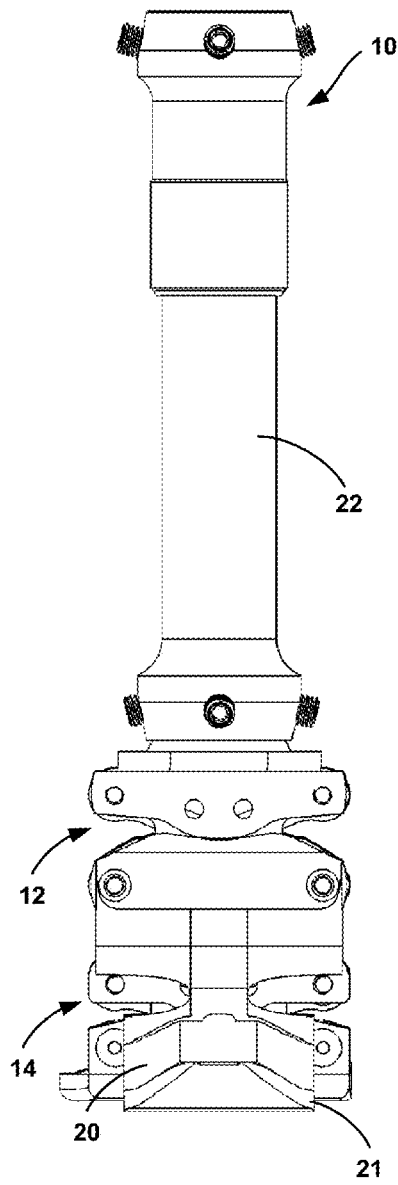
FIG. 8 is a rear view of the prosthetic device, according to the example embodiment of FIG. 1.
Figure 9:
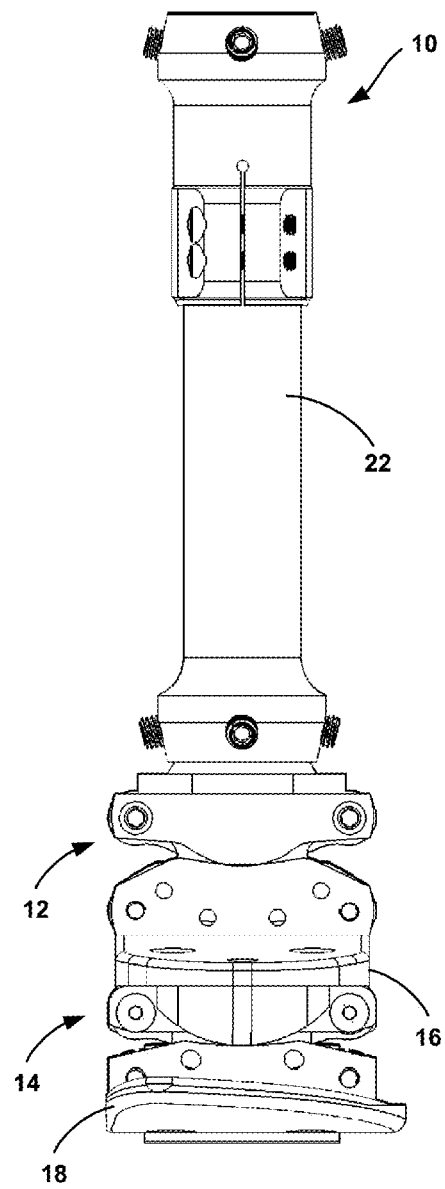
FIG. 9 is a front view of the prosthetic device, according to the example embodiment of FIG. 1.

FIG. 7 illustrates a side view of the prosthetic device 10, including the first linkage system 12, the second linkage system 14, the platform 16, the base 18, the hindfoot support 20, the hindfoot pad 21, and the prosthetic limb 22. FIG. 8 illustrates a rear view of the prosthetic device 10, including the first linkage system 12, the second linkage system 14, the hindfoot support 20, the hindfoot pad 21 and the prosthetic limb 22. Similarly, FIG. 9 illustrates a front view of the prosthetic device 10, including the first linkage system 12, the second linkage system 14, the platform 16, the base 18, and the prosthetic limb 22.

Figure 10:
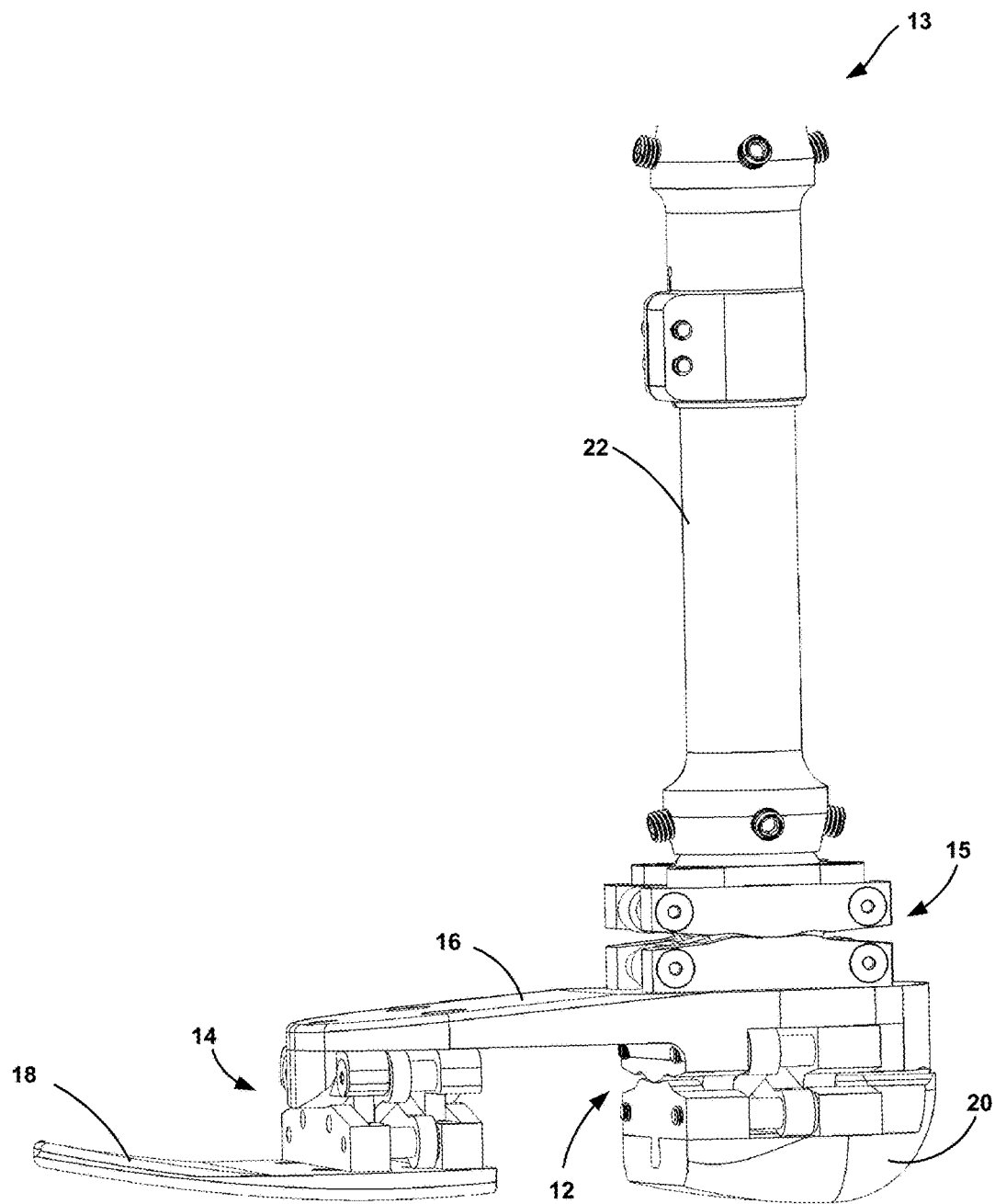
FIG. 10 is a perspective view of a prosthetic device, according to a second example embodiment.

FIG. 10 illustrates another prosthetic device 13 in accordance with another embodiment of the invention. As shown in FIG. 10, the prosthetic device 13 includes a first linkage system 12 and a second linkage system 14. The first linkage system 12 may be a hindfoot component of the prosthetic device 13, and the second linkage system 14 may be a forefoot component. The plane of rotation of the first linkage system 12 may be substantially parallel to the plane of rotation of the second linkage system 14. In other words, like components of the first linkage system 12 and the second linkage system 14 are facing the same direction, as shown in FIG. 10. The prosthetic device 13 may also include a platform 16 coupling the first linkage system 12 to the second linkage system 14. The prosthetic device 10 may further include a base 18 coupled to a lower portion of the second linkage system 14.

The prosthetic device 13 may further include a third linkage system 15 positioned between the platform 16 and the prosthetic limb 22. The third linkage system 15 may have a similar configuration to the first linkage system 12 and the second linkage system 14 (as described in relation to linkage system 11 in FIGS. 2-6). In particular, the third linkage system 15 may include (i) a third upper portion having a third contact surface, (ii) a third lower portion having a fourth contact surface, wherein the fourth contact surface contacts the third contact surface, (iii) a third tension bearing element with a first end pivotally coupled to a first end of the third lower portion and a second end pivotally coupled to a second end of the third upper portion, and (iv) a fourth tension bearing element with a first end pivotally coupled to a second end of the third lower portion and a second end pivotally coupled to a first end of the third upper portion. In such an example, the first upper portion 24 of the first linkage system 12 is coupled to the platform 16 and the third lower portion of the third linkage system is coupled to one of the platform 16 or the first upper portion 24 of the first linkage system 12.

In addition, the plane of rotation of the third linkage system 15 may be substantially perpendicular to the plane of rotation of the first linkage system 12 and the plane of rotation of the second linkage system 14. In particular, the plane of rotation of the third upper portion of the third linkage system 15 is perpendicular to the plane of rotation of the first upper portion of the first and second linkage systems. In such a configuration, the first linkage system 12 and the second linkage system 14 may enable medial-lateral movement, such as pronation and supination of the foot. The third linkage system 15 may enable dorsiflexion and plantarflexion of the foot. While three linkage systems are described herein, any number of linkage systems similar to linkage system 11 may be added to the prosthetic device 10 to improve stability of the wearer.

In a configuration including the third linkage system 15, the prosthetic limb 22 may be coupled to the third upper portion of the third linkage system 15. A bottom portion of the prosthetic limb 22 may include a connector portion that is configured to mate with a connector portion positioned on a top surface of the third upper portion of the third linkage system. Other connection mechanisms are possible as well.

Figure 11:
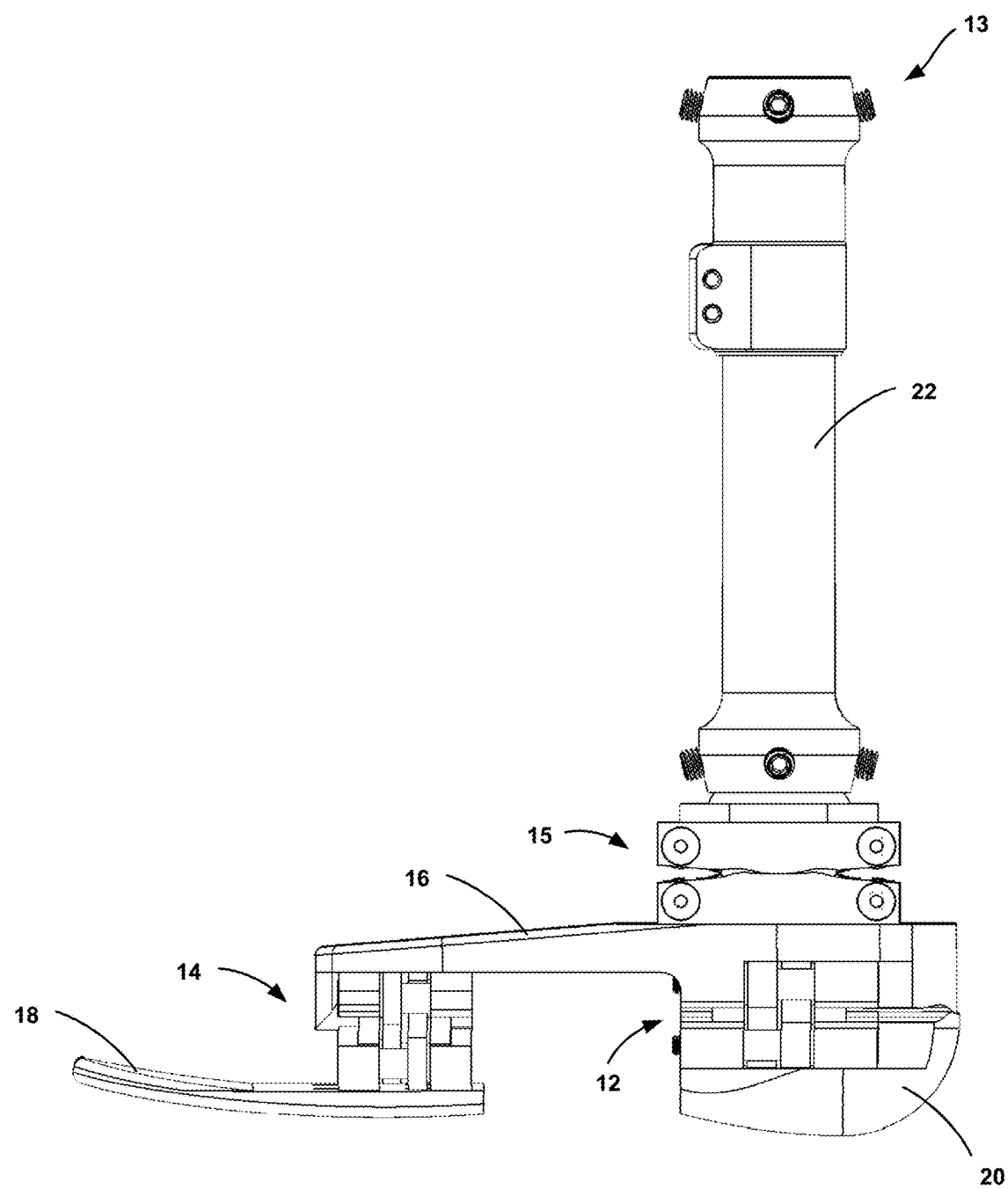
FIG. 11 is a side view of the prosthetic device, according to the example embodiment of FIG. 10.

FIG. 11 illustrates a side view of the prosthetic device 13, including the first linkage system 12, the second linkage system 14, the third linkage system 15, the platform 16, the base 18, the hindfoot support 20, and the prosthetic limb 22. FIG. 12 illustrates a rear view of the prosthetic device 13, including the first linkage system 12, the third linkage system 15, the base 18, the hindfoot support 20, and the prosthetic limb 22. Similarly, FIG. 13 illustrates a front view of the prosthetic device 13, including the second linkage system 14, the third linkage system 15, the platform 16, the base 18, and the prosthetic limb 22.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

We claim:

1. A prosthetic foot device comprising:
   a first linkage system and a second linkage system, each linkage system including:
   (i) a first upper portion having a first contact surface;
   (ii) a first lower portion having a second contact surface, wherein the second contact surface contacts the first contact surface;
   (iii) a first tension bearing element with a first end pivotally coupled to a first end of the first lower portion and a second end pivotally coupled to a second end of the first upper portion;
   (iv) a second tension bearing element with a first end pivotally coupled to a second end of the first lower portion and a second end pivotally coupled to a first end of the first upper portion;
   a platform having a top surface and a bottom surface, wherein the top surface of the platform is coupled to the first lower portion of the first linkage system, and wherein the bottom surface of the platform is coupled to the first upper portion of the second linkage system; and
   a base coupled to the first lower portion of the second linkage system.

2. The prosthetic foot device of claim 1, wherein the first contact surface of each linkage system comprises a convex surface, and wherein the second contact surface each linkage system comprises a concave surface.

3. The prosthetic foot device of claim 2, wherein a contact between the first contact surface and the second contact surface of each linkage system comprises an instantaneous center of rotation of the first upper portion with respect to the first lower portion.

4. The prosthetic foot device of claim 1, wherein the first contact surface of each linkage system and the second contact surface of each linkage system comprise a convex surface.

5. The prosthetic foot device of claim 1, wherein the first contact surface of each linkage system comprises a first material, and wherein the second contact surface of each linkage system comprises a second material that is different than the first material.

6. The prosthetic foot device of claim 1, wherein the base extends from the first lower portion of the second linkage system in a direction away from the first linkage system.

7. The prosthetic foot device of claim 1, wherein the second linkage system has a shorter length and a shorter height than a length and a height of the first linkage system.

8. The prosthetic foot device of claim 1, wherein each of the first linkage system and the second linkage systems further comprise:
   a third tension bearing element with a first end pivotally coupled to the first end of the first lower portion and a second end pivotally coupled to the second end of the first upper portion; and
   a fourth tension bearing element with a first end pivotally coupled to a second end of the first lower portion and a second end pivotally coupled to a first end of the first upper portion.

9. The prosthetic foot device of claim 1, wherein each of the first linkage system and the second linkage systems further comprise:
   a second upper portion having a third contact surface;
   a second lower portion having a fourth contact surface, wherein the third contact surface contacts the fourth contact surface, wherein the first end of the first tension bearing element is pivotally coupled to a first end of the second lower portion and a second end of the first tension bearing element is pivotally coupled to the second end of the first upper portion, and wherein the first end of the second tension bearing element is pivotally coupled to the second end of the first lower portion and the second end of the second tension bearing element is pivotally coupled to the first end of the second upper portion.

10. The prosthetic foot device of claim 1, wherein one or more of the first linkage system and the second linkage systems further includes at least one spring mechanism configured to return the first linkage system and/or the second linkage system to a position of repose when the device is unweighted.

11. The prosthetic foot device of claim 1, wherein the first upper portion of the first linkage system is configured to be coupled to a prosthetic limb or a legged robotic device.

12. The prosthetic foot device of claim 1, wherein a maximum angle between the first upper portion of the first linkage system and the first lower portion of the first linkage system is between about ten and about twenty degrees.

13. The prosthetic foot device of claim 1, wherein a maximum angle between the first upper portion of the second linkage system and the first lower portion of the second linkage system is between about twenty and about forty-five degrees.

14. The prosthetic foot device of claim 1, wherein a plane of rotation of the first upper portion of the first linkage system is parallel to a plane of rotation of the first upper portion of the second linkage system.

15. The prosthetic foot device of claim 1, further comprising a housing sized and shaped to surround the device.

16. The prosthetic foot device of claim 1, wherein the first tension bearing element and the second tension bearing element each comprise a bar or a cable.

17. The prosthetic foot device of claim 1, wherein a length to height ratio of each of the first linkage system and the second linkage system is greater than 1.5:1.

18. A prosthetic foot device comprising:
a first linkage system, a second linkage system, and a third linkage system, each linkage system including:
  (i) a first upper portion having a first contact surface;
  (ii) a first lower portion having a second contact surface, wherein the second contact surface contacts the first contact surface;
  (iii) a first tension bearing element with a first end pivotally coupled to a first end of the first lower portion and a second end pivotally coupled to a second end of the first upper portion;
  (iv) a second tension bearing element with a first end pivotally coupled to a second end of the first lower portion and a second end pivotally coupled to a first end of the first upper portion;
a platform having a top surface and a bottom surface, wherein the bottom surface of the platform is coupled to the first upper portion of the first linkage system, wherein the bottom surface of the platform is coupled to the first upper portion of the second linkage system, wherein the top of the platform is coupled to the first lower portion of the third linkage system, and wherein the plane of rotation of the third upper portion of the third linkage system is perpendicular to the plane of rotation of the first upper portion of the first and second linkage systems; and
a base coupled to the first lower portion of the second linkage system.

19. The prosthetic foot device of claim 18, further comprising a hindfoot support having an upper surface coupled to the first lower portion of the first linkage system.

20. The prosthetic foot device of claim 18, wherein the base extends from the first lower portion of the second linkage system in a direction away from the first linkage system.

* * * * *